United States Patent [19]

Comninellis et al.

[11] Patent Number: 4,582,942

[45] Date of Patent: Apr. 15, 1986

[54] PROCESS FOR THE MANUFACTURE OF AN ALDEHYDE

[75] Inventors: Christos Comninellis, Prilly; Eric Plattner, Seltisberg, both of Switzerland

[73] Assignee: Givaudan Corporation, Clifton, N.J.

[21] Appl. No.: 643,970

[22] PCT Filed: Dec. 19, 1983

[86] PCT No.: PCT/CH83/00145

§ 371 Date: Aug. 15, 1984

§ 102(e) Date: Aug. 15, 1984

[87] PCT Pub. No.: WO84/02522

PCT Pub. Date: Jul. 5, 1984

[30] Foreign Application Priority Data

Dec. 29, 1982 [CH] Switzerland .................. 7612/82
Nov. 3, 1983 [CH] Switzerland .................. 5934/83

[51] Int. Cl.$^4$ ........................................... C07C 47/542
[52] U.S. Cl. ................................. 568/426; 204/59 R; 204/78
[58] Field of Search ............... 204/78, 59 R; 568/426

[56] References Cited

U.S. PATENT DOCUMENTS

| | | | |
|---|---|---|---|
| 4,148,696 | 4/1979 | Halter | 204/59 R |
| 4,212,710 | 7/1980 | Halter | 204/78 |
| 4,212,711 | 7/1980 | Halter et al. | 204/78 |
| 4,277,318 | 7/1981 | Matlock | 204/78 |
| 4,298,438 | 11/1981 | Degner et al. | 204/78 |
| 4,387,007 | 6/1983 | Seiler | 204/59 R |
| 4,411,746 | 10/1983 | Degner | 204/78 |

FOREIGN PATENT DOCUMENTS

| | | |
|---|---|---|
| 175295 | 7/1903 | Fed. Rep. of Germany . |
| 2435985 | 2/1975 | Fed. Rep. of Germany . |
| 2948455 | 6/1981 | Fed. Rep. of Germany . |
| 3028757 | 9/1982 | Fed. Rep. of Germany . |
| 55-148781 | 11/1980 | Japan . |
| 56-020174 | 2/1981 | Japan . |

OTHER PUBLICATIONS

Ramaswamy et al., *J. Electrochem. Soc.*, Mar. 1963, pp. 202-204.

D. Pletcher, "Industrial Electrochemistry", p. 162, Chapman & Hall Ltd., London (1982).

Ch. Comninellis, et al., J. Electrochem. Soc. 129, No. 4, 749 (1982).

*Primary Examiner*—John F. Niebling
*Attorney, Agent, or Firm*—Robert F. Tavares

[57] ABSTRACT

Manufacture of p-tert. butyl-benzaldehyde (TBT) by oxidation with a $Mn^{3+}$ salt, which salt is generated by electrochemical oxidation of a $Mn^{2+}$ salt, and whereby the chemical oxidation and the electrochemical oxidation are carried out in separate reaction vessels.

24 Claims, No Drawings

PROCESS FOR THE MANUFACTURE OF AN ALDEHYDE

The invention is concerned with a process for the manufacture of p-tert.butylbenzaldehyde (TBB). This aldehyde is a known substance, especially as an intermediate.

The process comprises oxidizing p-tert.butyltoluene (TBT) with a $Mn^{3+}$ salt, which salt is generated by electrochemical oxidation of a $Mn^{2+}$ salt, and whereby the chemical oxidation and the electrochemical oxidation are carried out in separate reaction vessels.

The sulphate is preferably used as the manganese salt. However, the phosphate can also be used. This salt gives no problems at all with respect to electrochemical stability (i.e. cathodic as well as anodic), with respect to interference with organic materials and with respect to corrosion.

The electrochemical oxidation is conveniently carried out in moderately concentrated sulphuric acid, namely in 40% (5.3 molar) to 90% (16.6 molar), especially in 50% (7.1 molar) to 65% (10.3 molar), sulphuric acid.

The electrochemical oxidation is conveniently carried out at an elevated temperature, preferably in a temperature range of about 60° C. to 110° C., especially at 80° C. to 100° C. and particularly at about 85° C.

The concentration of the manganese salt in the inorganic phase conveniently amounts of 1 to 5 mol/l, especially 3.0 to 4.0 mol/l and particularly about 3 mol/l.

The anode material used can be in principle any electrode material which is stable under the process conditions, namely for example:

Vitreous graphite, lead, lead alloys, noble metals such as platinum or metals which are passive towards anodic corrosion (e.g. zirconium and tantalum) and which are coated with a noble metal (e.g. with palladium or ruthenium).

Lead alloys, for example those with a content of silver (e.g. Chromin from Blasberg, GFR) are especially preferred. In the electrolytes there are found in this manner Ag ions which act as the catalyst, namely the lower valued metal ions of a transition metal-redox pair with an oxidation potential greater than $Mn^{2+}/Mn^{3+}$. It has been found that the use of such lead alloys is especially economical, since the life of the electrodes is long (e.g. it can amount to 1 to 1½ years).

As the cathode material there is likewise used vitreous graphite, lead, lead alloys, noble metals such as platinum, but especially also lead or lead alloys (e.g. Chromin).

The reaction can be carried out in an undivided cell or in a cell which is divided by a porous diaphragm consisting of usual inert materials. The reaction is preferably carried out in a cell without a diaphragm. Although in the latter case it is convenient to carry out the reaction in a protective gas atmosphere (e.g. under nitrogen) in order to protect against explosive gas formation (from anodically-formed oxygen and cathodically-produced hydrogen), the gases which result in the reaction during the electrolysis can also simply be rarefied by the addition of a protective gas (e.g. nitrogen); however, rarefaction with air also leads to the prevention of the danger of explosion.

For the electrochemical oxidation there can be used essentially any conventional, especially commercially available, type of cell. Thus, for example, there can be used channel cells [flow cells] (in which the electrodes are arranged as a comb or as a package (stack) (in the form of plates, cylinders etc), these cells being preferred;

filter press cells (consisting of frames and plates);

trough (tank) cells (the stirring action required being realized by electrolyte circulation, by means of an inert gas or by means of rotating electrodes, etc.).

A preferred type of channel cell is, for example, that which has been described by D. Pletcher in Industrial Electrochemistry, Chapman & Hall (London, New York), (1982), 162.

As the cell material there can be used any inert material, but especially a synthetic polymeric material (e.g. polypropylene).

The current densities in the reaction in accordance with the invention conveniently lie at 100 to 600 $mA/cm^2$, especially at 300 to 500 $mA/cm^2$ (i.e. 3 to 5 $kA/m^2$).

The cell potential adjusts itself as a function of the composition of the electrolyte, the temperature and the geometry of the particular cell. It can, for example, assume a value of 2.5 to 4 V, especially of 2.5 to 3.0 V and particularly of about 3 V.

The oxidation of p-tert.butyltoluene is carried out in accordance with the invention with an electrochemically-generated $Mn^{3+}$ salt, but in a separate reaction vessel.

Thus, the reaction is preferably carried out in a three-phase system, namely: sulphuric acid/$Mn^{3+}$ (and $Mn^{2+}$) salt suspended therein/organic material.

The sulphuric acid concentration preferably amounts to 40% to 90%, especially 50% to 65% and particularly about 55%.

The content of manganese salts [$Mn^{+2}$ (traces) and $Mn^{+3}$] in the inorganic phase is conveniently at least 2.5 mol/l, thus, for example, it amounts to 3 to 4 mol/l, especially about 3 mol/l.

The organic material consists mainly of TBT, TBB and solvent. As solvents there come into consideration especially aliphatic hydrocarbons—e.g. heptanes, octanes, cyclohexane—as well as their chlorinated or fluorinated derivatives, e.g. methylene chloride, tetrachloro ethylene, perfluoro octane ($C_8F_8$), etc. These solvents have a sufficient dissolving power for TBT and its oxidation product; they are insoluble in the inorganic phases; their chemical stability vis-à-vis the reaction medium is satisfactory, and they can be separated readily from the reaction products. Octane and chlorinated aliphatics are preferred solvents. TBT is the especially preferred solvent.

The reaction is conveniently carried out at a temperature of 80° C. to 110° C., especially 90° C. to 100° C. and particularly at about 95° C.

It is advantageous to discontinue the chemical oxidation after a 40% or lower conversion, especially after a 20% to 30% conversion, of p-tert.butyltoluene, particularly in view of the danger of a loss of selectivity. This amounts in the optimum case to above 90%. Possible byproducts are, in particular, small amounts (e.g. about 3%) of the corresponding carboxylic acid.

The separation of the reaction product consisting essentially of TBB, $MnSO_4$, sulphuric acid and orgaic solvent into two inorganic phases (suspension of $MnSO_4.H_2O$ in sulphuric acid) and one organic phase can be carried out by filtration and decantation or by centrifugation. The separation of TBB and remaining organic material or solvent is conveniently carried out by distillation.

The TBT can thereupon be recycled.

Before recycling the inorganic phase, it is conveniently freed from residual organic material by means of steam and/or a gas. The easiest method is by stripping in columns in a countercurrent procedure.

The electrochemical oxidation is preferably carried out continuously. The chemical oxidation can be carried out continuously or discontinuously.

The electrolytic efficiency of the electrochemical process lies at about 70%.

The electrochemical oxidation of $Mn^{2+}$ to $Mn^{3+}$ per se is known from the literature; see, for example, J. Electrochem. Soc. 129 [4], 749-752 (1982).

It is also known that p-tert.butyltoluene can be directly oxidized electrochemically to p-tert.butylbenzaldehyde; see, for example, Japanese Patent Application Nos. 79/096296 and 79/56996 and DOS No. 2948455.

Further, it is known that aromatic hydrocarbons (e.g. xylenes or toluenes) can be oxidized using electrolytically-produced $Mn_2(SO_4)_3$; see, for example, German Patent Specification No. 175295, U.S. Pat. Nos. 4,212,710 and 4,212,711 and J. Electrochemical Society 110 [3], 202-204, (1963).

The parameters enumerated above, which enable the aldehyde obtainable in accordance with the invention to be manufactured selectively on a technical scale in an economical manner (i.e. inexpensively) can not be concluded from any of the aforementioned literature references. In this respect, the present process is also clearly superior to the process using $Ce^{4+}$ salts (see, for example, German Patent Specification No. 3028757). In comparison with this process, the following parameters in particular permit an economical process: lower atomic weight, price, electrolytic efficiency, concentration of the salt in the electrochemical oxidation~concentration in the chemical oxidation, stability of the solvent in the anode compartment, lower cell voltage, higher concentration of the salt during the electrochemical oxidation in the case in accordance with the invention, working-up of the (chemically) manufactured tert-.butylbenzaldehyde. A particular advantage of working with manganese salts is also to be seen, in that in the scope of the present invention it has been found that $Mn^{3+}$ is approximately 10 times less soluble than $Mn^{2+}$ in about 50% sulphuric acid; in other words, the danger of the reduction of $Mn^{3+}$ at the cathode is very much less during the electrochemical oxidation.

Thus, while the prior art provides a number of approaches to the problem, it does not provide a method which is selective and efficient enough to be commercially attractive for the manufacture of the aldehyde on a large scale.

EXAMPLE 1

Apparatus: undivided circulation-plate cell and container having a capacity of 1.5 l (channel cell).
Anode and cathode: Chromin (Blasberg), surface 182 cm².
Electrolyte:
 454 g $MnSO_4.H_2O$
 428 g $H_2O$,
 699 g $H_2SO_4$ (100%).
Temperature: 95°-100° C.
Amperage: 39 A.
Voltage: 2.5-3.0 V.

After electrolysis with a current amount of 3.58 F (96 A.h), there are obtained 725 g of $Mn_2(SO_4)_3.H_2SO_4.4H_2O$, the electrolytic efficiency amounts to 71.5% and the conversion relative to $Mn^{2+}$ is 95%.

The electrolyte is now added to a reaction vessel having a capacity of 1.5 l. 135 ml of water are added thereto while stirring within 10 minutes and the mixture is heated to 90° C. 360 g of TBT, heated to 60° C., are now added thereto in one portion, the temperature firstly dropping to 80° C. and thereupon rising to 95° C. The volume of the mixture amounts to 1.4 l. The mixture is stirred at 95° C. for 15 minutes and the liquid phases are sucked through a glass frit into a separating funnel which is thermostatized at 95° C. After separating the liquid phases, the inorganic phase is led back into the reaction vessel, stirred briefly and again sucked off. After three-fold sucking off, there are obtained 345 g of organic phase and 1.71 kg of inorganic phase, the latter containing a small amount of organic impurities.

The organic phase is washed with 180 g of a 5% $Na_2CO_3$ solution (containing 5% NaCl) and with 90 g of a 10% NaCl solution. The organic phase is distilled under a vacuum on a Vigreux column and gives 270 g of TBT as the lower boiling component and 83.6 g of TBB as the higher boiling component.

Yield:
TBT consumption: 360−270=90 g.
TBB distilled: 83.6 g (corresponding to 85% of theory).
Overall electrolytic efficiency: 71.5.80.86=57.8%.

After distilling off about 125 g of water and a small amount of organic material, the inorganic phase can be let back into the electrolysis cycle in place of fresh electrolyte.

EXAMPLE 2

Apparatus: undivided circulation-plate cell and container having a capacity of 1.5 l
Anode and cathode: Chromin (Blasberg), surface 182 cm².
Electrolyte:
 454 g $MnSO_4.H_2O$,
 428 g $H_2O$,
 699 g $H_2SO_4$ (100%)
Temperature: 95°-100° C.
Amperage: 39 A.
Voltage: 2.5-3.0 V.

After electrolysis with a current amount of 3.58 F (96 A.h), there are obtained 725 mg of $Mn_2(SO_4)_3.H_2SO_4.4H_2O$, the electrolytic efficiency amounts to 71.5% and the conversion relative to $Mn^{2+}$ is 95%.

360 g of TBT are heated to 90° C. in a 1.5 l reaction vessel. It is now added while stirring well within 1 to 1.5 hours to the oxidized electrolyte. 135 ml of water are added simultaneously to the reaction vessel. The temperature is held at 95° C. during the addition and the subsequent reaction time (40 minutes). The reaction mass is cooled to 60° C. and the liquid phases are thereupon sucked through a glass frit into a separating funnel which is thermostatized at 60° C. After separating the liquid phases, the inorganic phase is led back into the reaction vessel, stirred briefly and again sucked off. After three-fold sucking off, there are obtained 345 g of organic phase and 1.71 kg of inorganic phase, the latter containing a small amount of organic impurities.

The organic phase is washed at 60° C. with about 180 g of a 20% neutral $Na_2SO_4$ solution. This solution can be used several times by always bringing its pH-value to 7±0.5 with a small amount of 12% sodium hydroxide solution. The organic phase is distilled under a vacuum on a Vigreux column and gives 270 g of TBT as the lower boiling component and 86.0 g of TBB as the higher boiling component.

Yield:

TBT consumption: 360−270=90 g.

TBB distilled: 86.0 g (corresponding to 87% of theory).

Overall electrolytic efficiency: 71.5.83.2=59.5%. After distilling off about 125 g of water and a small amount of organic material, the inorganic phase can be led back into the electrolysis cycle in place of fresh electrolyte.

EXAMPLE 3

In the plant the electrochemical oxidation $Mn^{2+} \rightarrow Mn^{3+}$ (in $H_2SO_4$) can be effected continuously in a first reaction system, and the reaction mixture so obtained then transferred into a second reaction vessel for the realisation of the chemical oxidation TBT→TBB in the 3-phase system: sulphuric acid/$Mn^{3+}$ salt suspended therein/organic solvent, e.g. TBT. The reaction product is separated into 2 inorganic phases (suspension of $MnSO_4.H_2O$ in sulphuric acid) and an organic phase by centrifugion. The inorganic phases are then stripped of residual organic material in a packed column of residual organic material (e.g. by steam) by application of the countercurrent technique, and are thereafter transferred back to the first reaction system. The organic phase is washed with alkali (as described above) and separated into crude TBB and organic solvent by distillation. The TBT, TBB and water recovered by stripping are added to the system, e.g. to the second reaction vessel.

We claim:

1. A process for the manufacture of p-tert-butylbenzaldehyde, which process comprises chemically oxidizing p-tert-butyltoluene with a $Mn^{3+}$ salt, wherein:
   (a) said $Mn^{3+}$ salt is generated by electrochemical oxidation of a $Mn^{2+}$ salt,
   (b) the chemical oxidation and the electrochemical oxidation are carried out in separate reaction vessels,
   (c) the chemical oxidation is carried out at temperature of 80° C. to 110° C.,
   (d) the electrochemical oxidation is carried out at a temperature of 80° C. to 100° C., and
   (e) the electrochemical oxidation is carried out using a current density greater than or equal to 100 mA/cm$^2$.

2. A process according to claim 1 wherein the $Mn^{2+}$ salt is manganese sulphate.

3. A process according to claims 1 or 2 wherein the electrochemical oxidation is carried out
   (a) in 40% (5.3 molar) to 90% (16.6 molar) sulphuric acid, and
   (b) with the $Mn^{2+}$ salt present at a concentration of 1 to 5 mol/l.

4. A process according to claim 3 wherein there is used a cell potential of about 2.5 to 4 V.

5. A process according to claim 1 wherein the electrochemical oxidation is carried out using
   (a) an anode made from vitreous graphite, lead, a lead alloy, a noble metal or a metal which is passive to anodic corrosion and which is coated with a noble metal, and
   (b) a cathode made from vitreous graphite, lead, a lead alloy, or a noble metal.

6. A process according to claim 5 wherein
   (a) the anode material is a lead alloy, and
   (b) the cathode material is lead or a lead alloy.

7. A process according to claim 6 wherein the anode and cathode consist of the same material.

8. A process according to claim 7, wherein a lead-silver alloy is used as the electrode material.

9. A process according to claim 8 wherein the $Mn^{2+}$ salt is manganese sulfate.

10. A process according to claims 5, 6, 7, 8, or 9 wherein the electrochemical oxidation is carried out in an undivided electrolysis cell.

11. A process according to claim 10 wherein the reaction is carried out under an inert atmosphere.

12. A process according to claim 8 wherein the cell is a filter press cell, a trough cell or a channel cell.

13. A process according to claim 12 wherein the cell is a channel cell.

14. A process according to claims 12 or 13 wherein the cell consists of an inert synthetic polymeric material.

15. A process according to claim 1 wherein the oxidation of p-tert-butyltoluene is carried out in a three-phase system wherein two of the three phases consists of a suspension of solid $Mn^{3+}$ salt, or $Mn^{2+}$ and $Mn^{3+}$ salt in sulphuric acid which suspension corresponds to the system $Mn^{3+}$ ($Mn^{2+}$)/$H_2SO_4$ of the electrochemical oxidation and the third phase is an organic material.

16. A process according to claim 15 wherein
   (a) the concentration of $Mn^{3+}$ salt or $Mn^{2+}$ and $Mn^{3+}$ salt is greater than or equal to 2.5 mol/l,
   (b) the concentration of the sulphuric acid is from 40% (5.3 molar) to 90% (16.6 molar), and
   (c) the organic material is p-tert-butyltoluene.

17. A process according to claim 16 wherein the reaction is carried out under an inert atmosphere.

18. A process according to claim 17 wherein
   (a) the concentration of $Mn^{3+}$ salt or $Mn^{2+}$ and $Mn^{3+}$ salt is 3 to 4 mol/l,
   (b) the concentration of sulphuric acid is 50% (7.1 molar) to 65% (10.3 molar),
   (c) the temperature is from 90° C. to 100° C., and
   (d) the inert atmosphere is nitrogen.

19. A process according to claims 15, 16, 17 or 18 wherein the oxidation is discontinued at a 40% or less conversion of p-tert-butyltoluene.

20. A process according to claim 19 wherein the conversion of p-tert-butyltoluene is 20% to 30%.

21. A process according to claim 19 wherein
   (a) the reaction products are separated into the inorganic phases and organic phase by means of filtration, decantation or centrifigation,
   (b) the inorganic phases are treated with steam or an inert gas to remove organic materials, and
   (c) the inorganic phases are recycled.

22. A process according to claim 19 wherein the oxidation is carried out continuously or discontinuously.

23. A process according to claim 14 wherein the electrochemical oxidation is carried out
   (a) in 50% (7.1 molar) to 65% (10.3 molar) sulphuric acid,
   (b) with the $Mn^{2+}$ salt present at a concentration of 3.0 to 4.0 mol/l,
   (c) with a current density of 300 to 500 mA/cm$^2$, and
   (d) with a cell potential of 2.5 to 3.0 V.

24. A process according to claims 4, 9, or 23 wherein the oxidation is carried out continuously.

* * * * *

UNITED STATES PATENT AND TRADEMARK OFFICE
CERTIFICATE OF CORRECTION

PATENT NO. : 4,582,942

DATED : April 15, 1986

INVENTOR(S) : Christos Comninellis et al.

It is certified that error appears in the above-identified patent and that said Letters Patent is hereby corrected as shown below:

In claim 12, column 6, line 15, correct "claim 8" to read --claim 10--.

On the title page, in the ABSTRACT, correct the first line "Manufacture of p-tert. butyl-benzaldehyde (TBT)..." to read --Manufacture of p-tert.-butyl-benzaldehyde (TBB)...--.

Signed and Sealed this

Fourteenth Day of January, 1992

Attest:

HARRY F. MANBECK, JR.

Attesting Officer      Commissioner of Patents and Trademarks